US012778578B2

(12) United States Patent
DeGregorio

(10) Patent No.: US 12,778,578 B2
(45) Date of Patent: Nov. 3, 2026

(54) WEDGE LOCK NEEDLE HOLDER

(71) Applicant: John DeGregorio, Pittsburgh, PA (US)

(72) Inventor: John DeGregorio, Pittsburgh, PA (US)

( * ) Notice: Subject to any disclaimer, the term of this patent is extended or adjusted under 35 U.S.C. 154(b) by 368 days.

(21) Appl. No.: 18/142,550

(22) Filed: May 2, 2023

(65) Prior Publication Data

US 2023/0346366 A1 Nov. 2, 2023

Related U.S. Application Data

(60) Provisional application No. 63/337,466, filed on May 2, 2022.

(51) Int. Cl.
*A61B 17/06* (2006.01)

(52) U.S. Cl.
CPC .............................. *A61B 17/06061* (2013.01)

(58) Field of Classification Search
CPC .. A61B 17/06061; A61B 17/062-0625; A61B 17/0482; A61B 17/0491; A61B 17/0483; A61B 2017/301-308
USPC .................................................. 606/144-148
See application file for complete search history.

(56) References Cited

U.S. PATENT DOCUMENTS 2,363,334 A 11/1944 Jones
3,709,226 A 1/1973 Santos
4,580,567 A 4/1986 Schweitzer et al.
4,621,640 A 11/1986 Mulhollan et al.
5,015,250 A 5/1991 Foster
5,300,082 A 4/1994 Sharpe et al.
5,370,658 A * 12/1994 Scheller ............. A61B 17/2909 606/174
5,391,174 A 2/1995 Weston
5,454,819 A 10/1995 Knoepfler
(Continued)

FOREIGN PATENT DOCUMENTS

CN 104605905 5/2015
DE 199016261 2/1991
(Continued)

OTHER PUBLICATIONS

International Search Report for corresponding International Patent Application No. PCT/US23/20747 dated Jul. 26, 2023.
(Continued)

*Primary Examiner* — Elizabeth Houston
*Assistant Examiner* — Serenity A Miller
(74) *Attorney, Agent, or Firm* — Reed Smith LLP; Matthew P. Frederick; Cheryl L. Gastineau

(57) ABSTRACT

A suture needle holder device and method including a handle assembly and an elongate body including an outer hollow cannula and an inner push rod. A distal end of the outer hollow has at a suture release slot between two fenestrations configured as suture needle entry and exit points. The suture needle holder device is configured to be operable between an open position wherein the inner push rod is proximal to the at least two fenestrations, a closing position wherein a tapered face of the inner push rod is configured to engage a curved suture needle, an arrestment position wherein the inner push rod is disposed at the most remote distal position within the outer hollow cannula, and a snap-back position wherein a first spring within the distal end of an outer hub case causes a retraction of the outer hollow cannula and inner push rod.

8 Claims, 16 Drawing Sheets

(56) References Cited

U.S. PATENT DOCUMENTS

| | | | |
|---|---|---|---|
| 5,630,832 | A | 5/1997 | Giordano et al. |
| 5,893,877 | A | 4/1999 | Gampp, Jr et al. |
| 6,818,005 | B2 | 11/2004 | Kupferschmid et al. |
| 8,568,427 | B2 | 10/2013 | Nobles et al. |
| 9,649,107 | B2 | 5/2017 | Brecher et al. |
| D838,555 | S | 1/2019 | Gauss et al. |
| D838,921 | S | 1/2019 | Dunbar |
| 10,610,215 | B2 | 4/2020 | Anderson et al. |
| 10,709,443 | B2 | 7/2020 | Anderson et al. |
| 10,736,623 | B2 | 8/2020 | Anderson et al. |
| 10,779,812 | B2 | 9/2020 | Anderson et al. |
| 10,835,236 | B2 | 11/2020 | Anderson et al. |
| 10,888,314 | B2 | 1/2021 | Kurd et al. |
| 10,918,379 | B2 | 2/2021 | Kurd et al. |
| 10,952,722 | B2 | 3/2021 | Kurd et al. |
| 11,045,186 | B2 | 6/2021 | Belman et al. |
| 11,090,042 | B2 | 8/2021 | Kurd et al. |
| 11,259,798 | B2 | 3/2022 | Limon et al. |
| 2011/0190794 | A1 | 8/2011 | Dingler et al. |
| 2014/0311272 | A1 * | 10/2014 | Jakoubek ........... A61B 17/2909 74/491 |
| 2019/0133569 | A1 | 5/2019 | Malkowski |
| 2022/0160347 | A1 * | 5/2022 | Deblois .............. A61B 17/0469 |

FOREIGN PATENT DOCUMENTS

| | | |
|---|---|---|
| DE | 202011052176 | 5/2012 |
| EP | 0571057 | 11/1993 |
| EP | 0688535 | 12/1995 |
| WO | 199944517 | 9/1999 |

OTHER PUBLICATIONS

European search report dated Jan. 23, 2026 for corresponding European Patent Application No. 23799952.9.

* cited by examiner

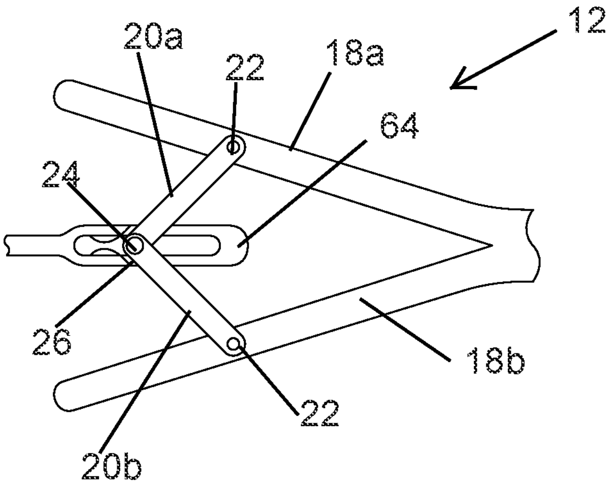
FIG. 4A
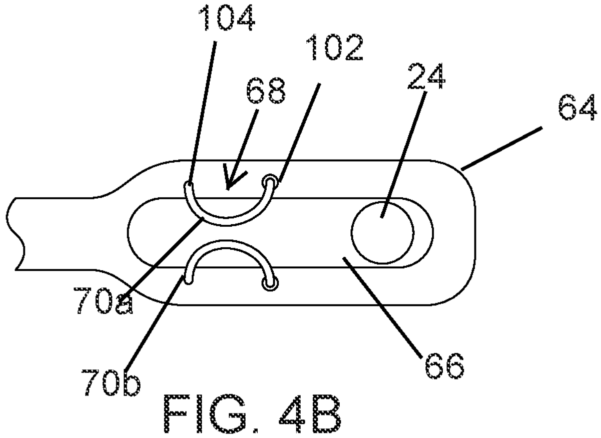
FIG. 4B
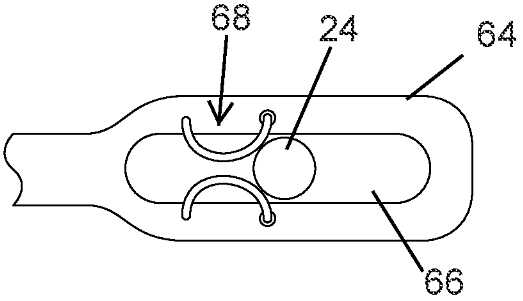
FIG. 4C
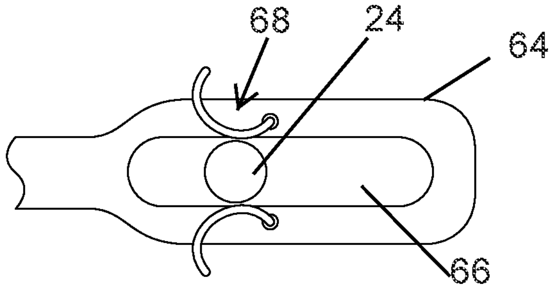
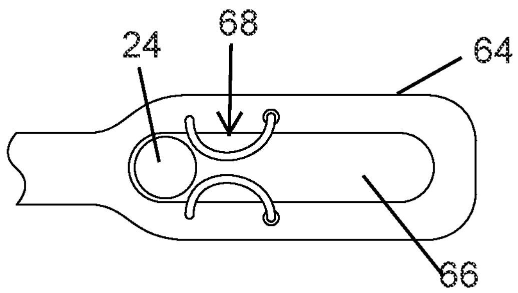
FIG. 4D
FIG. 4E

WEDGE LOCK NEEDLE HOLDER

CROSS-REFERENCE TO RELATED APPLICATIONS

This application claims the benefit under 35 U.S.C. § 119(e) of the earlier filing date of the U.S. Provisional Application No. 63/337,466, filed May 2, 2022, the entirety of which is incorporated by reference herein.

BACKGROUND

Needle holders are surgical instruments which may be used to hold a needle with an attached suture in a fixed orientation to permit the needle to be placed or driven through tissue. Historically, needle holders work on the mechanism of integrated clamps or prolonged hand pressure which lock the needle in place as long as required to maintain the needle in it desired position.

Minimal invasive surgery has made surgical incisions, exposures and corridors smaller and often deeper. The space at the targeted surgical site is limited. The bulk of the jaws, the obstruction of view from the two shanks and the mass of the shanks of a conventional needle holder limit or preclude their use in minimally invasive surgery (MIS). Single shaft needle holders are known for use in MIS.

SUMMARY

In some embodiments a suture needle holder device comprises a handle assembly comprising a proximal handle end, a distal handle end, and first and second opposed handle bodies each pivotally connected to a handle drive arm at a first end of each handle drive arm, wherein the handle assembly further comprises a common drive pin pivotally connected to a second end of each drive arm; an elongate body connected with the handle assembly at the distal handle end, the elongate body comprising a proximal elongate body end portion and a distal elongate body end portion, the elongate body comprising: an outer hollow cannula comprising a hollow interior, a proximal hollow cannula end portion and a distal hollow cannula end portion; wherein the proximal hollow cannula end portion comprises a cannula hub comprising a cylindrical side wall, a hollow interior, and at least one spring-loaded detent pin disposed radially through the cylindrical side wall, wherein the distal hollow cannula end portion comprises at least two fenestrations and a suture release slot connecting the at least two fenestrations, and wherein a first one of the at least two fenestrations is configured as a suture needle entry point, and a second one of the at least two fenestrations is configured as a suture needle exit point; an inner push rod comprising a proximal push rod portion and a distal push rod portion, the inner push rod arranged for longitudinal displacement within the hollow interior of the outer hollow cannula, wherein the proximal push rod portion comprises a longitudinal slot and a spring gate comprising laterally opposed springs disposed within the longitudinal slot, wherein the drive pin is configured for longitudinal displacement within the longitudinal slot of the inner push rod upon compression of the first and second handle bodies towards one another, the inner push rod further comprising an inner rod hub comprising a proximal inner rod hub portion and a distal inner rod hub portion and configured for longitudinal displacement within the hollow interior of the cannula hub, wherein the distal push rod portion comprises a wedge shape comprising a tapered face configured to engage a curved suture needle inserted between the suture needle entrance point and the suture needle exit point; and an outer hub case comprising a side wall, a hollow interior, a proximal outer hub case portion and a distal outer hub case portion, wherein the cannula hub and the inner rod hub are arranged for longitudinal displacement within the hollow interior of the outer hub case, and a first spring is disposed within the hollow interior of the outer hub case at the distal outer hub case portion; wherein the suture needle holder device is configured to be operable between an open position wherein the inner push rod is proximal to the at least two fenestrations, a closing position wherein the tapered face of the inner push rod is configured to engage the curved suture needle, an arrestment position wherein the inner push rod is disposed at the most remote distal position within the outer hollow cannula, and a snap-back position wherein the first spring within the distal outer hub case portion causes a retraction of the outer hollow cannula and inner push rod.

In some embodiments, when in the open position, the first and second opposed handle bodies are in an un-compressed position, the drive pin is disposed within the longitudinal slot proximal of the spring gate, and the outer cannula hub is locked into the outer hub case by the at least one spring-loaded detent pin.

In some embodiments, wherein an inner surface of the sidewall of the outer hub case further comprises at least one recess configured to engage the at least one spring-loaded detent pin, when in the open position.

In some embodiments, wherein the inner rod hub further comprises a proximal flange on the proximal inner rod hub portion and at least one groove or recess on the distal inner rod hub on an outer surface of the distal inner rod portion configured to engage the at least one spring-loaded detent pin, and further comprising a second spring disposed within the hollow interior of the outer hub case at the proximal outer hub case portion between the proximal flange and the cannula hub.

In some embodiments, when in the closing position, the first and second opposed handle bodies are in a compressed position, the drive pin is configured to engage a proximal end of the spring gate, and the outer cannula hub is locked into the outer case via the at least one spring-loaded detent pin.

In some embodiments, when in the arrestment position, the outer cannula hub is locked into the outer case by the at least one spring-loaded detent pin. In some embodiments, wherein the tapered face of the inner push rod further comprises a longitudinal grooved recess configured to seat the curved suture needle, when in the arrestment position. In some embodiments, when in the snap-back position, the drive pin is distal of the spring gate.

In some embodiments of using embodiments of the disclosure, a method of suturing comprises providing a suture needle holder device comprising: a handle assembly comprising opposed handle bodies operatively connected to a drive pin; an elongate body connected with the handle assembly and comprising an outer hollow cannula comprising distal hollow cannula end portion including at least two fenestrations comprising an entrance fenestration and an exit fenestration and a suture release slot, and an inner push rod operatively connected to the drive pin and comprising a distal push rod portion comprising a tapered face; an outer hub case at a proximal end of the elongate body; inserting a curved suture needle through the entrance fenestration such that a distal tip of the needle extends through the exit fenestration, wherein the suture needle holder device is an open position and the inner push rod is proximal to the entrance and exit fenestrations; compressing the handle assemblies together until the tapered face of the inner push rod engages and locks the curved suture needle, placing the distal hollow cannula end portion of the suture needle holder device adjacent tissue to be sutured; over-compressing the handle assemblies together retracting the outer hollow cannula and inner push rod proximally driving the curved suture needle into the tissue in a snap-back position of the needle holder device.

In some embodiments, a proximal push rod portion of the inner push rod comprises a longitudinal slot and a spring gate comprising laterally opposed springs disposed within the longitudinal slot, the drive pin is configured for longitudinal displacement within the longitudinal slot, wherein the step of compressing the handle assemblies together further comprises driving the drive pin distally within the longitudinal slot.

In some embodiments, the inner push rod further comprising an inner rod hub and the outer cannula hub comprises an outer cannula hub at proximal end thereof, wherein when in the open position, the drive pin is disposed within the longitudinal slot proximal of the spring gate, and the outer cannula hub is locked into the outer hub case by at least one spring-loaded detent pin.

In some embodiments, when in the closing position, the first and second opposed handle bodies are in a compressed position, the drive pin is configured to engage a proximal end of the spring gate, and the outer cannula hub is locked into the outer case via the at least one spring-loaded detent pin. In some embodiments, when in an arrestment position, the outer cannula hub is locked into the outer case by the at least one spring-loaded detent pin. In some embodiments, wherein the tapered face of the inner push rod further comprises a longitudinal grooved recess configured to seat the curved suture needle, when in the arrestment position.

In some embodiments, wherein the inner rod hub further comprises at least one groove or recess on the inner rod hub configured to engage the at least one spring-loaded detent pin, wherein the inner rod hub and the outer cannula hub are locked together by the at least one spring-loaded detent pin when in the when the needle device is in the snap-back position. In some embodiments, when in the snap-back position, the drive pin is distal of the spring gate.

BRIEF DESCRIPTION OF THE DRAWINGS

The disclosed embodiments will hereinafter be described in conjunction with the appended drawings, provided to illustrate and not to limit the disclosed embodiments, wherein like designations denote like elements.

FIG. 4A is a partial top view of a handle assembly of a needle holder according to various embodiments of the disclosure.

FIGS. 4B, 4C, 4D and 4E show partial top views of the proximal end of the inner push rod in open, closing, arrestment point and snap-back positions, respectively.

DETAILED DESCRIPTION

Figure 1:
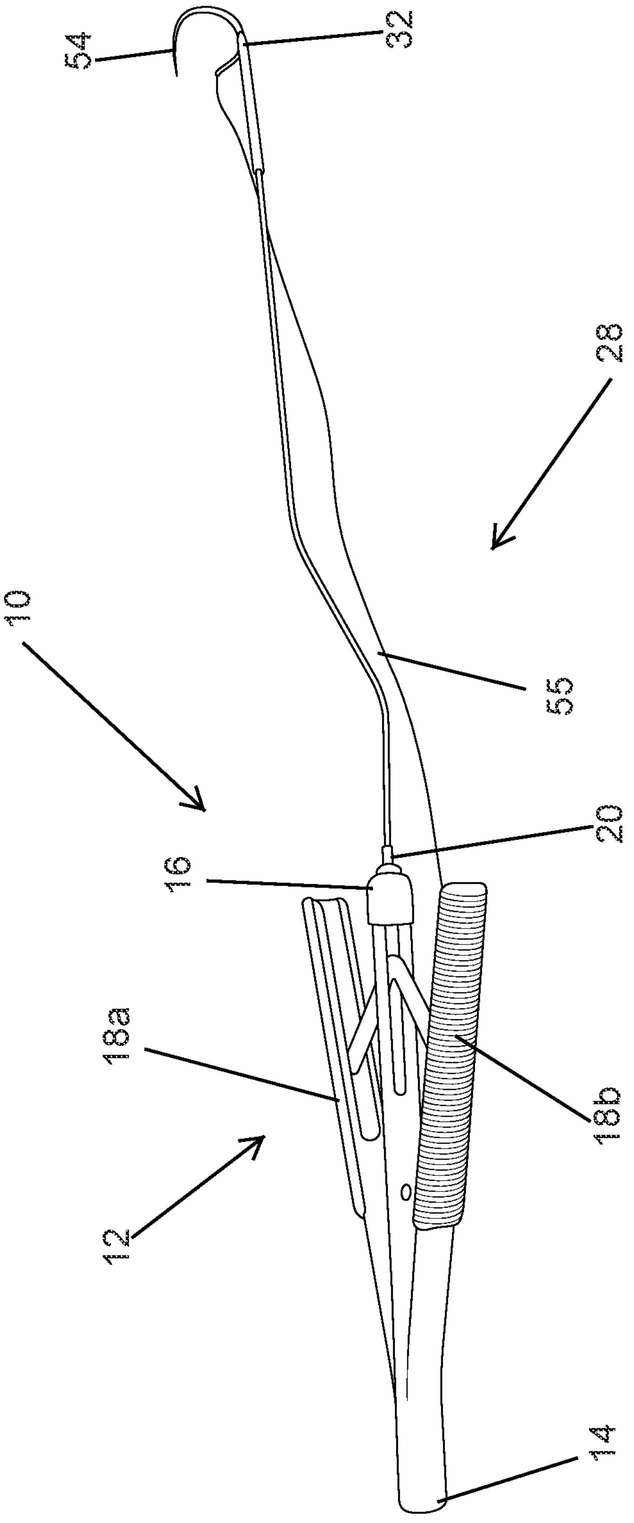
FIG. 1 shows a perspective view of a needle holder according to various embodiments of the disclosure.

Various embodiments of the novel systems, apparatuses, and methods disclosed herein are described more fully hereinafter with reference to the accompanying drawings. This disclosure can, however, be embodied in many different forms and should not be construed as limited to any specific structure or function presented throughout this disclosure. Rather, these embodiments are provided so that this disclosure will be thorough and will fully convey the scope of the disclosure to those skilled in the art. Based on the teachings herein, one skilled in the art would appreciate that the scope of the disclosure can be intended to cover any embodiment of the novel systems, apparatuses, and methods disclosed herein, whether implemented independently of, or combined with, any other embodiment of the disclosure. For example, an apparatus may be implemented or a method may be practiced using any number of the embodiments set forth herein. In addition, the scope of the disclosure can be intended to cover such an apparatus or method that can be practiced using other structure, functionality, or structure and functionality in addition to or other than the various embodiments of the disclosure set forth herein. It should be understood that any embodiment disclosed herein may be implemented by one or more elements of a claim.

Although particular embodiments are described herein, many variations and permutations of these embodiments fall within the scope of the disclosure. Although some benefits and advantages of the preferred embodiments are mentioned, the scope of the disclosure can be not intended to be limited to particular benefits, uses, and/or objectives. The detailed description and drawings are merely illustrative of the disclosure rather than limiting, the scope of the disclosure being defined by the appended claims and equivalents thereof.

It will be recognized that while certain embodiments of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations may be understood and effected by those skilled in the art in practicing the claimed disclosure, from a study of the drawings, the disclosure and the appended claims.

Henceforth, unless indicated otherwise herein, the term “proximal” means proximal with respect to the user of the device and “distal” means distal with respect to the user of the device.

Embodiments of the disclosure may be suture needle holders particularly useful in minimally invasive surgical procedures. Actuation of the instruments involves simple opposed finger movement which obviates the typical difficult rotational wrist movement necessary for use of typical needleholders. Other embodiments include agnostic needle and suture selection for use and in-situ needle repositioning without limits to suturing techniques.

In certain embodiments, a low distal mass single shaft needle holder allows for multiple suture placement, reloading and re-positioning of the needle with snap drive capability as well as agnostic needle and suture selection is described herein. Devices in accordance with this disclosure address the limitations identified in known devices.

The needle holder device described herein will now be described with reference to FIGS. 1-11F. Embodiments of needle holder 10 may include a handle assembly 12 comprising a proximal handle end 14, a distal handle end 16, and first and second opposed handle bodies 18*a*, 18*b* each pivotally connected to a handle drive arm 20*a*, 20*b* at a first end 22 of each handle drive arm 20*a*, 20*b*. In other embodiments, the handle assembly 12 may further include a common drive pin 24 pivotally connected to a second end 26 of each drive arm 20*a*, 20*b*.

In certain embodiments, needle holder 10 may further include a two-piece shaft assembly or elongate body 28 connected with the handle assembly 12 at the distal handle end 16. The elongate body 28 may include a proximal elongate body end portion 30 and a distal elongate body end portion 32. The elongate body 28 may further include an outer hollow cannula 34 and an inner push rod 35, which may be hollow or solid, arranged for longitudinal displacement within a hollow interior 36 of outer hollow cannula 34 distally along a longitudinal axis A of the outer hollow cannula 34. In some embodiments, outer hollow cannula 34 may further include a proximal hollow cannula end portion 38 and a distal hollow cannula end portion 40.

In some embodiments, proximal hollow cannula end portion 38 may include a cannula hub 42 comprising a cylindrical side wall 44, a hollow interior 46, and at least one spring-loaded detent pin 48 each disposed radially through a corresponding radial through-hole 49 in the cylindrical side wall 44. While, the embodiments illustrated in e.g. FIG. 3A include two opposed spring-loaded detent pins 48 and two radial through-holes 49, other non-illustrated embodiments contemplate one or three or more spring-loaded detent pins 48 and radial through-holes 49.

In certain embodiments, the distal hollow cannula end portion 40 may include at least two openings or fenestrations 50*a*, 50*b* and a suture release slot 52 connecting the fenestrations 50*a*, 50*b*. A first one of the at least two fenestrations 50*a* is configured as a suture needle entry point, and a second one of the at least two fenestrations 50*b* is configured as a suture needle exit point for a curved suture needle 54 having a curved profile and connected to a suture 55.

In certain embodiments, the at least two fenestrations 50*a*, 50*b* may be arranged on the outer surface of the outer hollow cannula 34 and radially open to the interior 36 of outer hollow cannula 34. The at least two fenestrations 50*a*, 50*b* may be arranged along an axis parallel to the longitudinal axis A of elongate body 28 such that second fenestration 50*b* is arranged along the longitudinal axis more distally than first fenestration 50*a*. In some embodiments, suture release slot 52 may be substantially U-shaped and extend between first fenestration 50*a* and second fenestration 50*b* on one side of outer hollow cannula 34. In other embodiments, first fenestration 50*a*, forming the needle entrance point, may have a substantially oblong oval first shape while second fenestration 50*b*, forming the needle exit point, may be smaller than first fenestration 50*a* and have a substantially circular shape. In some embodiments, outer hollow cannula 34 may further include a lobe 56 formed between first fenestration 50*a* and second fenestration 50*b* and defined by slot 52. Slot 52 may intersect only a portion of fenestrations 50*a*, and 50*a* to define lobe 56 to capture a curved suture needle 54. An interior surface of lobe 56 may be contoured to approximate the inner curvature of a curved suture needle 54 inserted between first fenestration 50*a* and second fenestration 50*b*.

Figure 9:
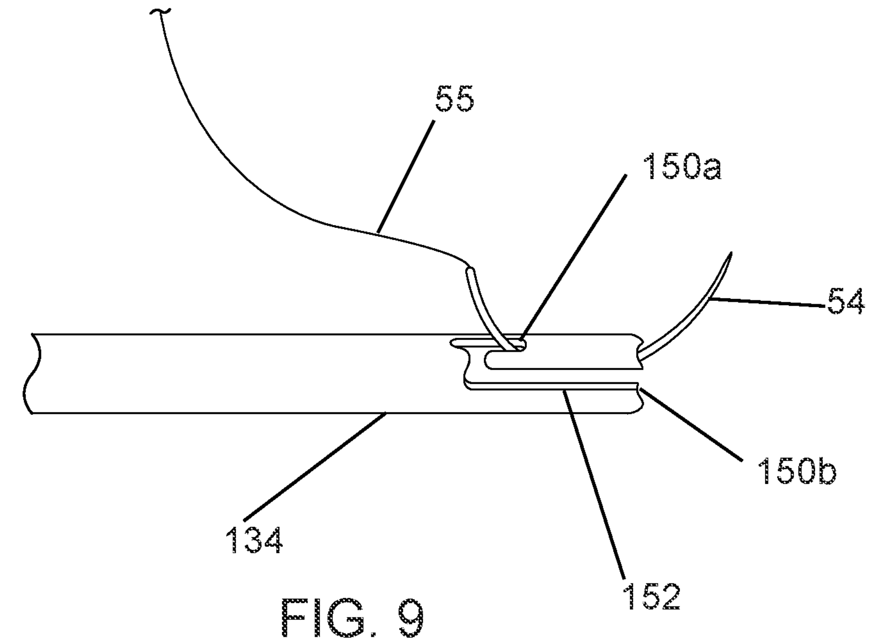
FIG. 9 shows a partial side view of the distal end of the needle holder according to various embodiments of the disclosure with a single fenestration and open end.
Figure 10:
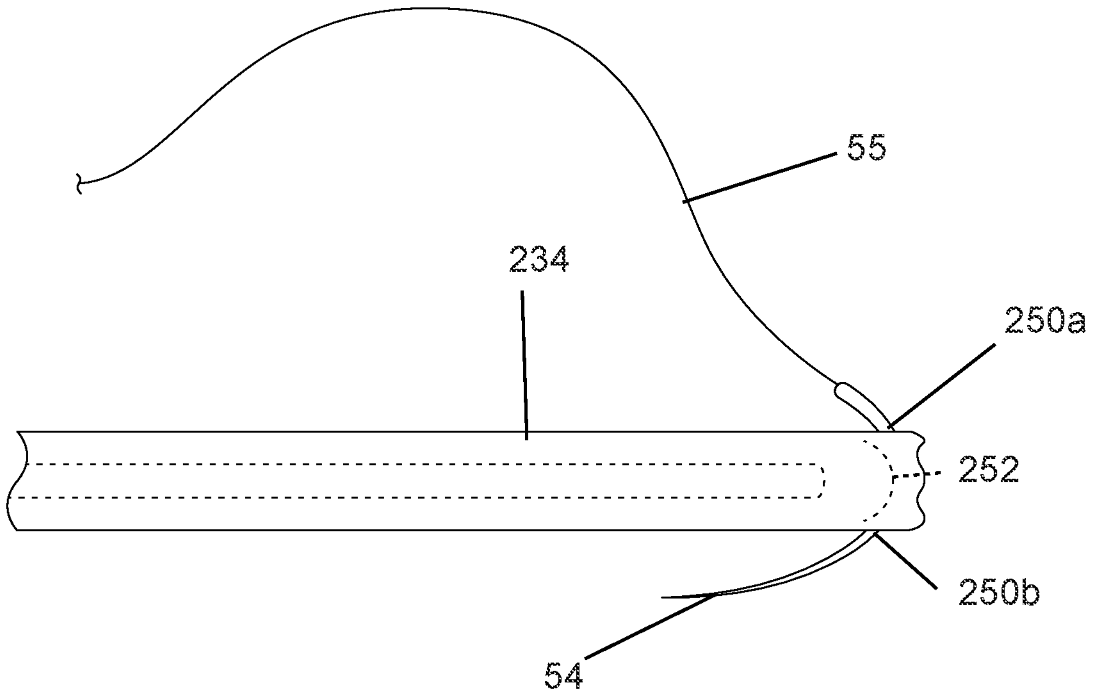
FIG. 10 shows a partial side view of the distal end of the needle holder according to various embodiments of the disclosure with a single fenestration and open end.

Alternative embodiments of the needle holder are shown in FIGS. 9 and 10. Like the earlier-described embodiment the curved suture needle 54 may be captured by two holes or fenestrations, an exit point and entry point with a suture release slot therebetween. In these alternative embodiments, the placement of the suture release slot is modified. In FIG.

9, the outer hollow cannula 134 may have an open distal end forming the second fenestration 150*b* with the suture release slot 152 extending between a first fenestration 150*a* and the second fenestration. In FIG. 10, the exit and entrance fenestrations 250*a*, 250*b* are spaced radially across the outer hollow cannula 234 with the curved suture release slot 252 extending there between. In embodiments, the exit and entrance fenestrations 250*a*, 250*b* and suture release slot 252 may be aligned perpendicular or at any angle to longitudinal axis A.

Figure 8A:
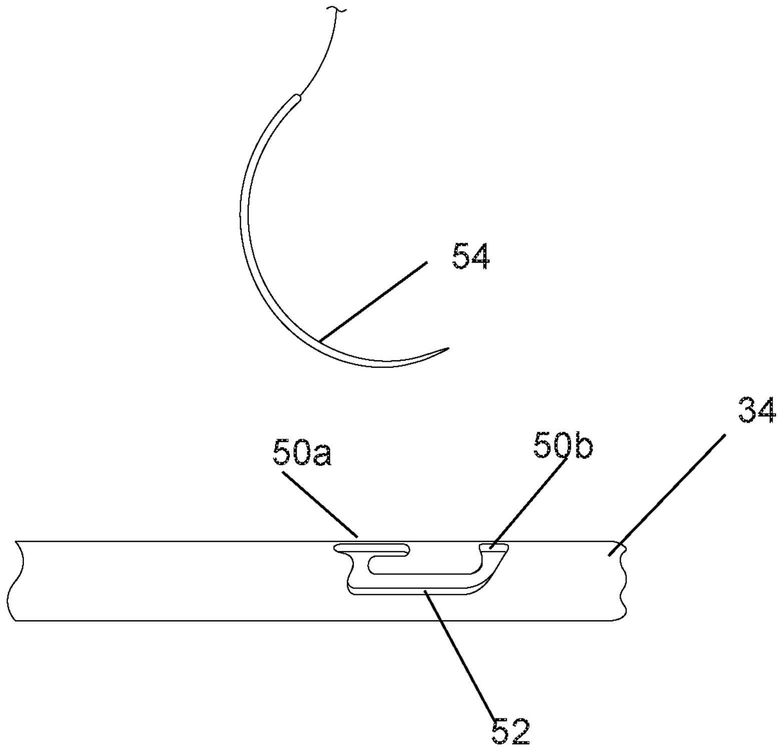
FIGS. 8A, 8B and 8C show partial side views of the distal end of the needle holder according to various embodiments of the disclosure in fenestrations fully opened, needle in fenestrations, needle releases positions.
Figure 8B:
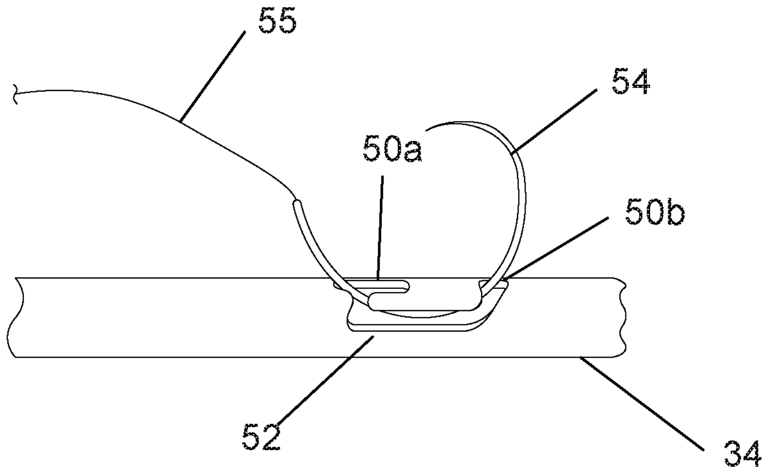
Figure 8C:
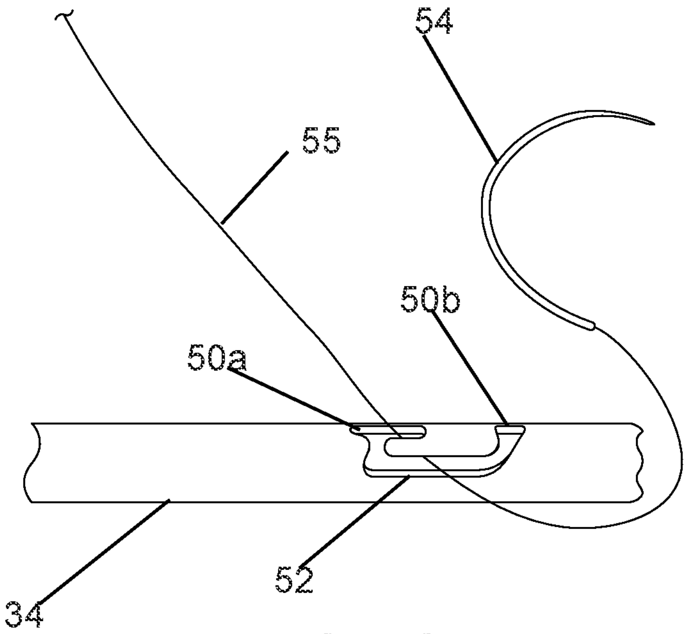

In a further embodiment, FIG. 8A shows the first and second fenestrations 50*a*, 50*b* in fully opened position before a needle 54 is inserted. FIG. 8B shows the first and second fenestrations 50*a*, 50*b* with a needle 54 inserted and the tip of the needle pointed proximally toward the handle assembly 12. Suture release slot 52 between the first and second fenestrations 50*a*, 50*b* allows the suture 55 that is attached to the needle 54 to be released from the device (FIG. 8C).

In some embodiments, inner solid push rod 35 may include proximal push rod portion 60 and a distal push rod portion 62. Inner push rod 35 arranged for longitudinal displacement within the hollow interior 36 of outer hollow cannula 34. Proximal push rod portion 35 may include a flattened portion 64 having an oval longitudinal slot 66. In certain embodiments, a spring gate 68 comprising laterally opposed springs 70*a*, 70*b* may be disposed within the longitudinal slot 66, wherein the drive pin 24 is configured for longitudinal displacement distally within the longitudinal slot 66 of the inner push rod 35 upon compression of the first and second handle bodies 18*a*, 18*b* towards one another. In embodiments, laterally opposed arrestment springs 70*a*, 70*b* may be resilient semi-circular hinge elements pivotally connected to flattened portion 64 at a proximal end of the spring gate 68. Alternatively, laterally opposed springs may be resilient semi-circular hinge elements which may be connected to the inner push rod at both proximal and distal ends of the spring gate 68. In other embodiments laterally opposed springs may be unitarily formed resilient portions of inner push rod projecting inwardly into the longitudinal slot 66. The inwardly projecting, unitarily formed portions may be formed from machining and/or may be made thinner than the remainder of the flattened portion 64 for increased malleability and spring-like function.

In some embodiments, inner push rod 35 may further include an inner rod hub 72 comprising a proximal inner rod hub portion 74 and a distal inner rod hub portion 76. Inner push rod 35 may be configured for longitudinal displacement within the hollow interior 46 of the cannula hub 42. In certain embodiments, distal push rod portion 62 may have a wedge shape comprising a tapered face 78 configured to engage a curved suture needle 54 inserted between the suture needle entrance point and the suture needle exit point. The tapered face 78 of the inner push rod 35 may include a holding grooved recess 80 configured to seat the curved suture needle 54. In certain embodiments, the tapered face 78 and holding grooved recess 80 may have diamond dust, carbon steel or other surface alterations to enhance the grip on the needle 54.

In some embodiments, needle holder 10 may further include an outer hub case 82 comprising a side wall 84, a hollow interior 86, a proximal outer hub case portion 88 and a distal outer hub case portion 90 which may be cone-shaped. Cannula hub 42 and the inner rod hub 72 may be arranged for longitudinal displacement within the hollow interior 86 of the outer hub case 82. In some embodiments, first spring 92 is disposed within the hollow interior 86 of the outer hub case 82 at the distal outer hub case portion 90.

In certain embodiments, needle holder 10 may be configured to be operable between an open position wherein the inner push rod 35 is proximal to the at least two fenestrations 50*a*, 50*b*, a closing position wherein the tapered face 78 of the inner push rod 35 engages the curved suture needle 54, an arrestment position wherein the inner push rod 35 is disposed at the most remote distal position within the outer hollow cannula 34, and a snap-back position wherein the first spring 92 within the distal outer hub case portion 90 causes a retraction of the outer hollow cannula 34 and inner push rod 35.

In certain embodiments, in the open position, the first and second opposed handle bodies 18*a*, 18*b* are in an un-compressed position, the drive pin 24 is disposed within the longitudinal slot 66 proximal of the spring gate 68, and the outer cannula hub 42 is locked into the outer hub case 82 by the at least one spring-loaded detent pin 48.

In some embodiments, in inner surface 94 of the sidewall 84 of the outer hub case 82 further comprises at least one hold-point recess 96 configured to engage the at least one spring-loaded detent pin 48, when in the open position.

Figure 2A:
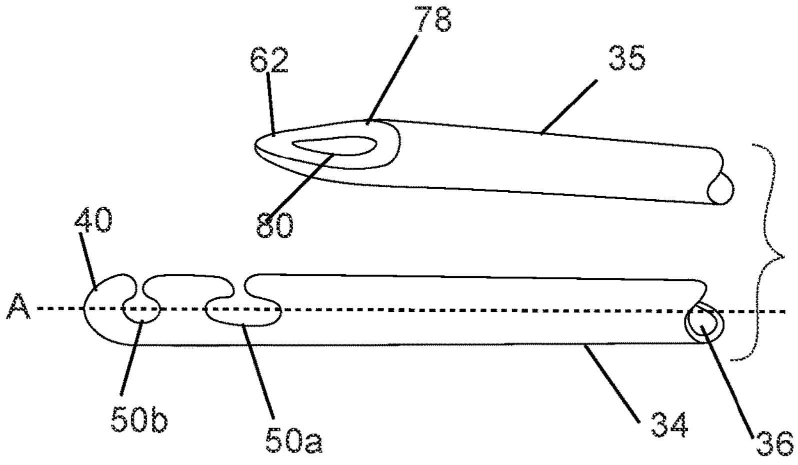
FIG. 2A shows a detail perspective view of the distal ends of the outer hollow cannula and inner push rod of the needle holder according to various embodiments of the disclosure.
Figure 2B:
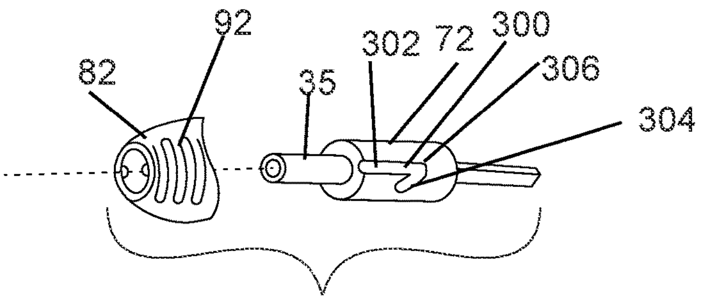
FIG. 2B shows a detail view of the distal end of the outer cannula hub and the inner rod hub of the needle holder according to various embodiments of the disclosure.
Figure 2C:
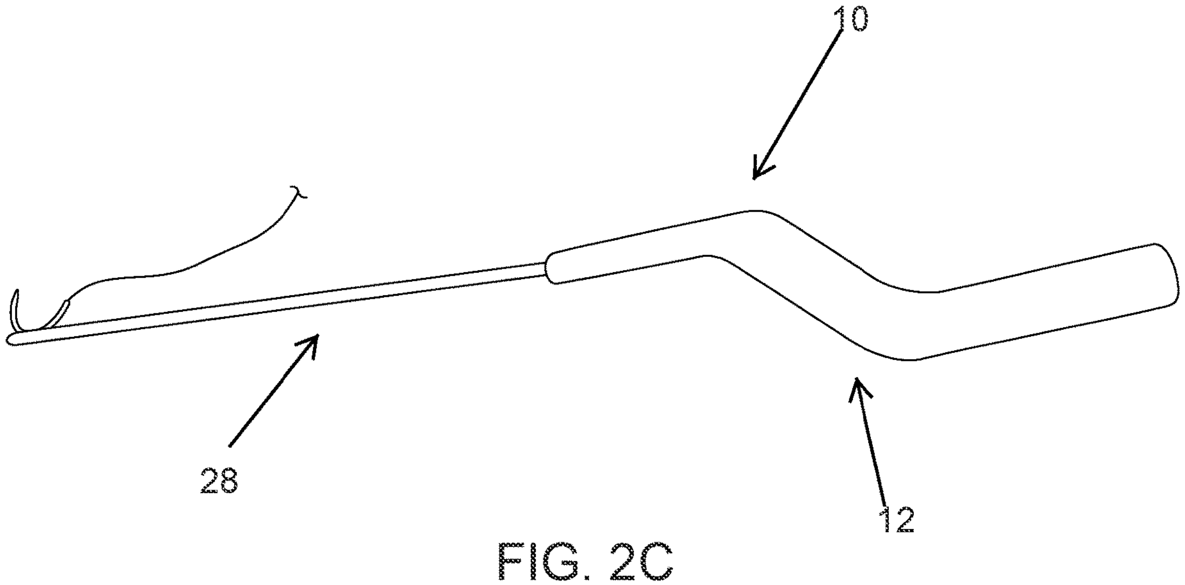
FIG. 2C shows a perspective view of a needle holder according to various embodiments of the disclosure.
Figure 2E:
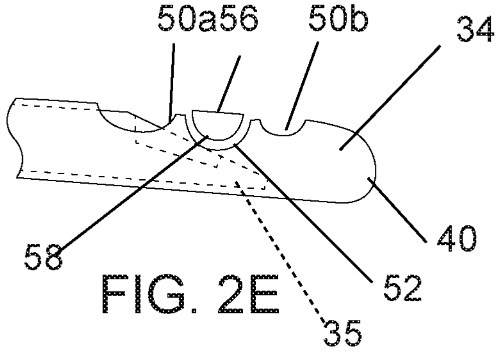
FIG. 2E shows a detail view of the distal end of the outer hollow cannula and inner push rod of the needle holder in the closing position.
Figure 2D:
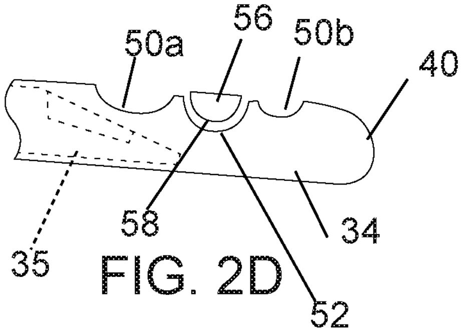
FIG. 2D shows a detail view of the distal end of the outer hollow cannula and inner push rod of the needle holder in the open position.
Figure 2F:
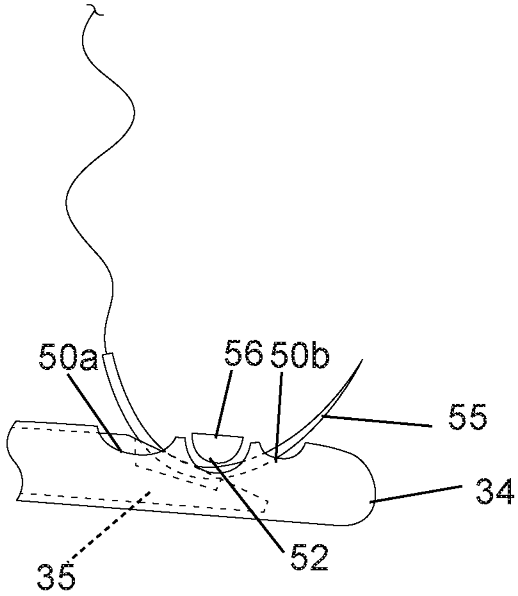
FIG. 2F shows a detail view of the distal end of the outer hollow cannula and inner push rod of the needle holder in an intermediate inserted position.
Figure 2G:
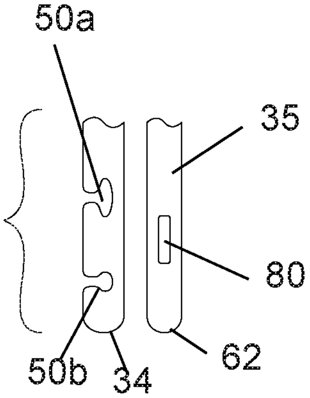
FIG. 2G shows a detail side top view of the distal ends of the outer hollow cannula and inner push rod of the needle holder according to various embodiments of the disclosure.
Figure 2H:
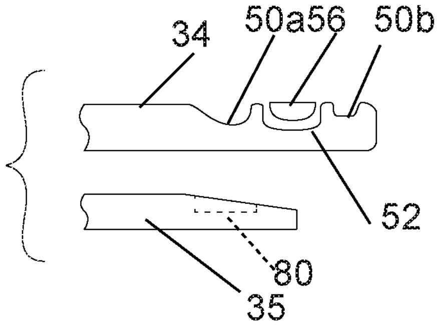
FIG. 2H shows a detail side view of the distal ends of the outer hollow cannula and inner push rod of the needle holder showing relative positions in the open position.
Figure 2I:
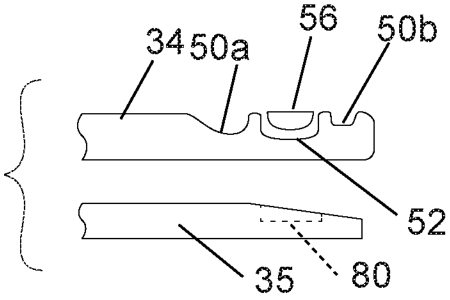
FIG. 2I shows a detail side view of the distal ends of the outer hollow cannula and inner push rod of the needle holder showing relative positions in the arrestment position.
Figure 3A:
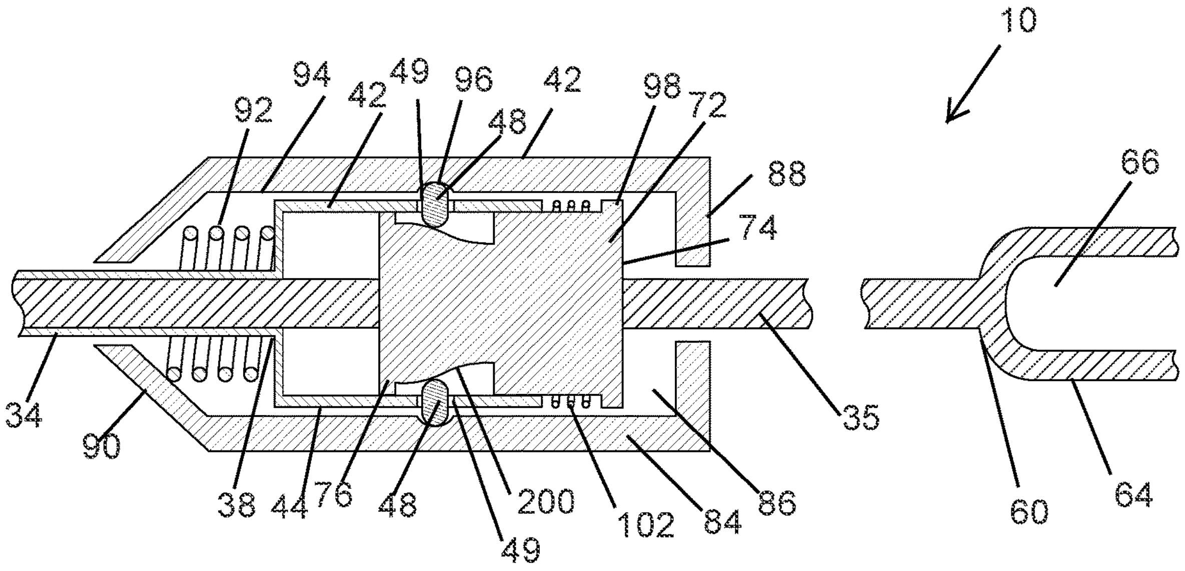
FIG. 3A is a partial cross-sectional side view of a needle holder according to various embodiments of the disclosure.
Figure 3B:
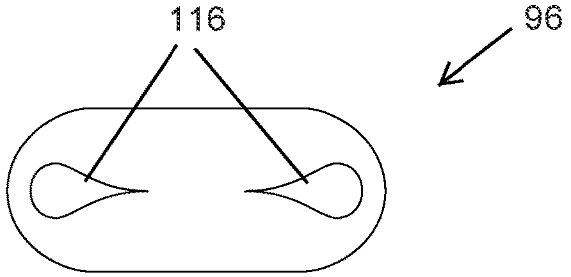
FIG. 3B is radial schematic view showing details of a hold-point recess according to various embodiments of the disclosure.
Figure 3C:
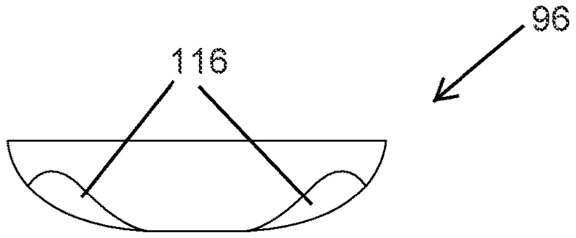
FIG. 3C is cross-sectional schematic view showing details of the hold-point recess according to various embodiments of the disclosure.
Figure 5A:
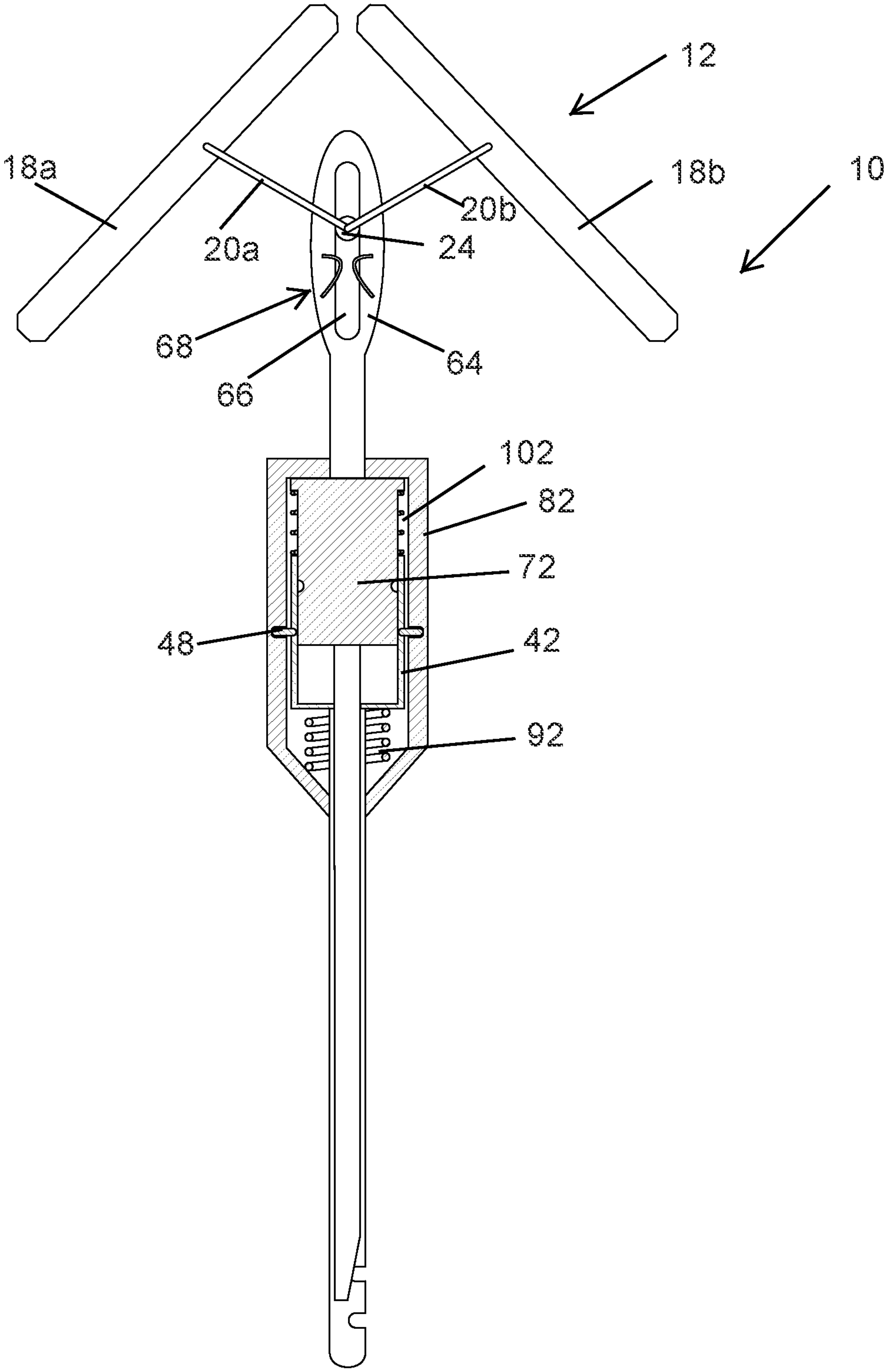
FIGS. 5A, 5B, 5C and 5D show cross-sectional top views of the needle holder according to various embodiments of the disclosure in open, closing, arrestment point and snap-back positions, respectively.

In further embodiments, the inner rod hub 72 may further include a proximal flange 98 on the proximal inner rod hub portion 74 and at least one groove or recess 100 on an outer surface of the inner rod hub 35. Each at least one groove or recess 100 may be configured to engage a corresponding one of the at least one spring-loaded detent pin 48. A second spring 102 may be disposed within the hollow interior 86 of the outer hub case 82 at the proximal outer hub case portion 88 between the proximal flange 98 and the cannula hub 42. The at least one groove or recess 100 may be a substantially hemispherical shaped recess 100 (FIGS. 5A-6). Alternatively, the at least one groove or recess may be at least one contoured groove 200 (FIG. 3A) of variable depth on opposite sides of the outer surface of the distal inner rod hub portion 76, wherein the depth of contoured groove substantially decreases from a proximal portion 202 of the groove 200 to a distal portion 204 of the groove 200. Another alternative embodiment is shown in FIG. 2*b* which shows the at least one groove or recess may be at least one substantially check-mark shaped groove 300 having a longer longitudinally leg 302, a shorter angled leg 304 and an apex 306 there between, wherein a corresponding spring-loaded detent pin 48 is configured to engage the longer longitudinally leg 302 when in the open and closing positions, the apex 306 when in the arrestment position and the shorter angled leg 304 when in the snap-back position. The various embodiment described herein including the grooves or recesses 100, 200 and 300 which facilitate the snap-back operation described herein.

Referring to the embodiment shown in FIG. 5A, when in the open position, the first and second opposed handle bodies 18*a*, 18*b* are un-compressed, the inner push rod 35 is retracted from the most distal fenestration Sob and is at its most proximal position due to the first and second opposed handle bodies 18*a*, 18*b* being in the widest spread position. In this position, the tip of the needle 54 can be inserted in the least distal openings 50*a* on the outer hollow shaft 34 and passed partially through the next distal opening 50*b* because the distal inner rod hub portion 76 does not interfere with positioning of the needle 54 being placed through both openings 50*a*, 50*b* (FIG. 5A.). In the open position, the spring loaded detent pins 48 engage hold-point recesses 96 in the side wall 84 of the outer hub case 82. This locks the outer cannula hub 42 to the outer hub case 82. The fenestration 50*a*, 50*b* are unobstructed.

Figure 5B:
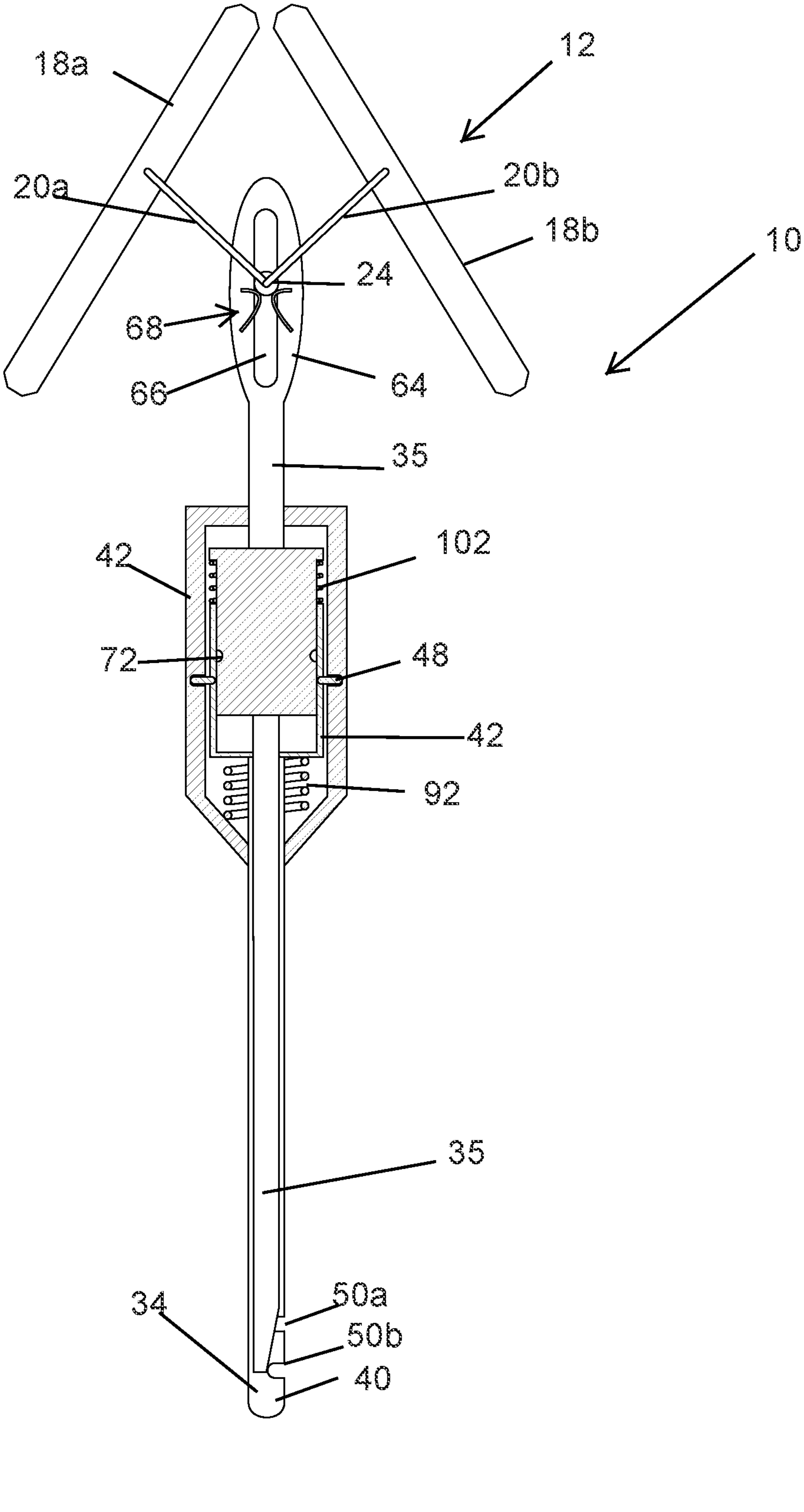
Figure 6:
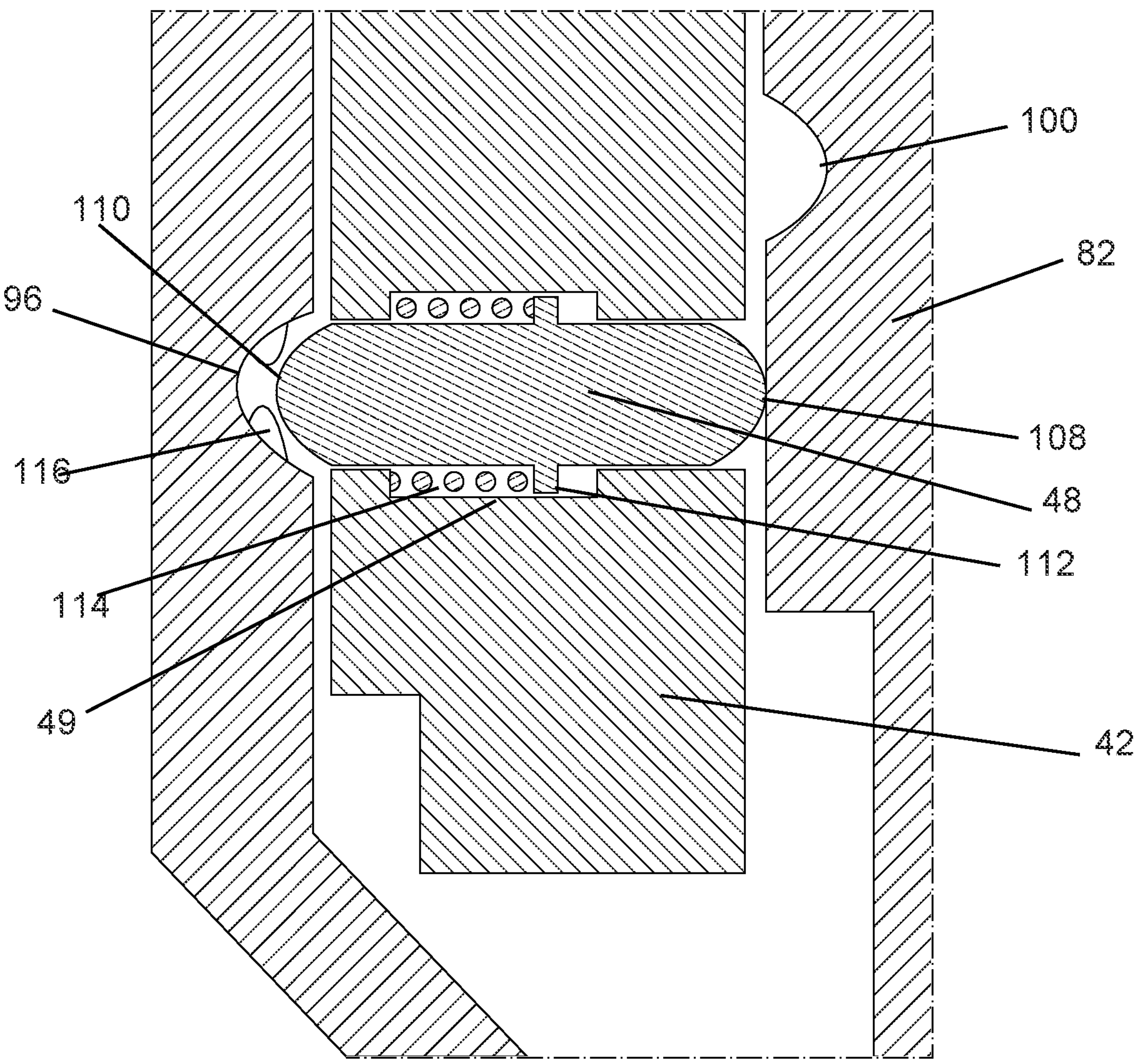
FIG. 6 shows a detail cross-sectional top views of the needle holder according to various embodiments of the disclosure.
Figure 7A:
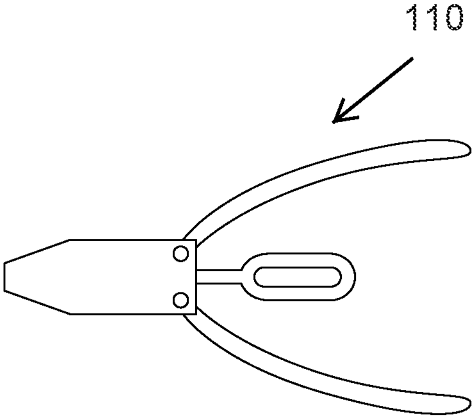
FIGS. 7A and 7B show top and side views, respectively of a handle assembly according to various embodiments of the disclosure.
Figure 7B:
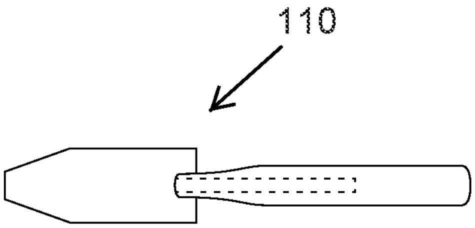
Figure 7C:
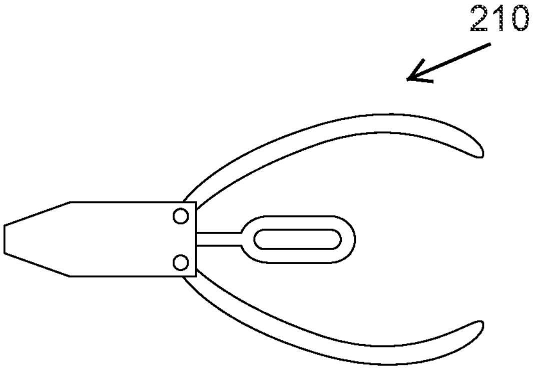
FIGS. 7C and 7D show top and side views, respectively of a handle assembly according to various embodiments of the disclosure.
Figure 7D:
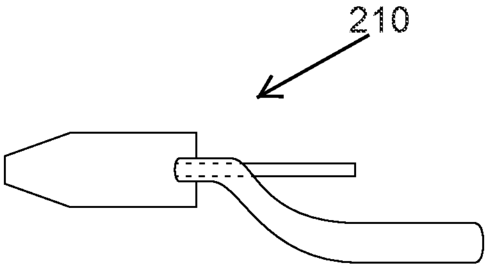
Figure 7E:
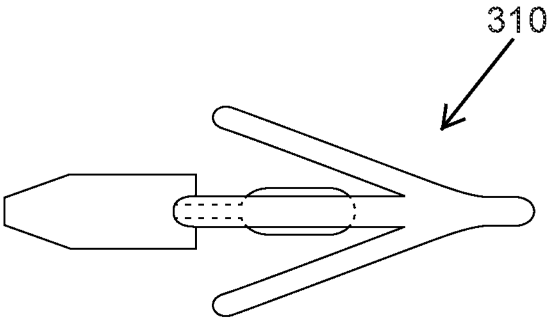
FIGS. 7E and 7F show top and side views, respectively of a handle assembly according to various embodiments of the disclosure.
Figure 7F:
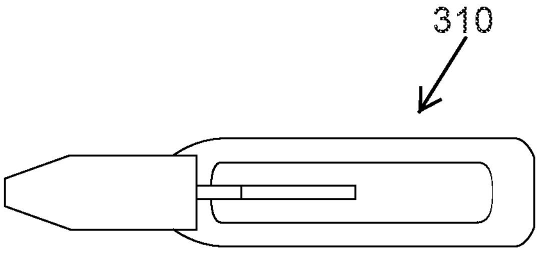

Referring to the embodiment shown in FIG. 5B, when in the closing position, the first and second opposed handle bodies 18*a*, 18*b* may be in a compressed position, the drive pin 24 may engage a proximal end 104 of the spring gate 68. The outer cannula hub 34 may be locked into the outer hub case 82 via the at least one spring-loaded detent pin 48. When the first and second opposed handle bodies 18*a*, 18*b* are compressed, the inner push rod 35 is advanced distally, the distal push rod portion reduces the apertures, i.e. cross-section area, of the openings 50*a*, 50*b*. The leading edge of the tapered face 78 engages the outer curvature of the needle 54 that has been placed into it and partially through the fenestrations 50*a*, 50*b* in the outer hollow cannula 34 (FIG. 5B) and compresses the needle against the hollow cannula end portion 40. Second spring 102 is compressed as the first and second opposed handle bodies 18*a*, 18*b* are closed. The compressive state of the first spring 92 is unchanged as first and second opposed handle bodies 18*a*, 18*b* are closed. The working length between the distal end 82 of outer hub case 82 and the distal end 40 of the outer cannula hub 34 is unchanged.

Figure 5C:
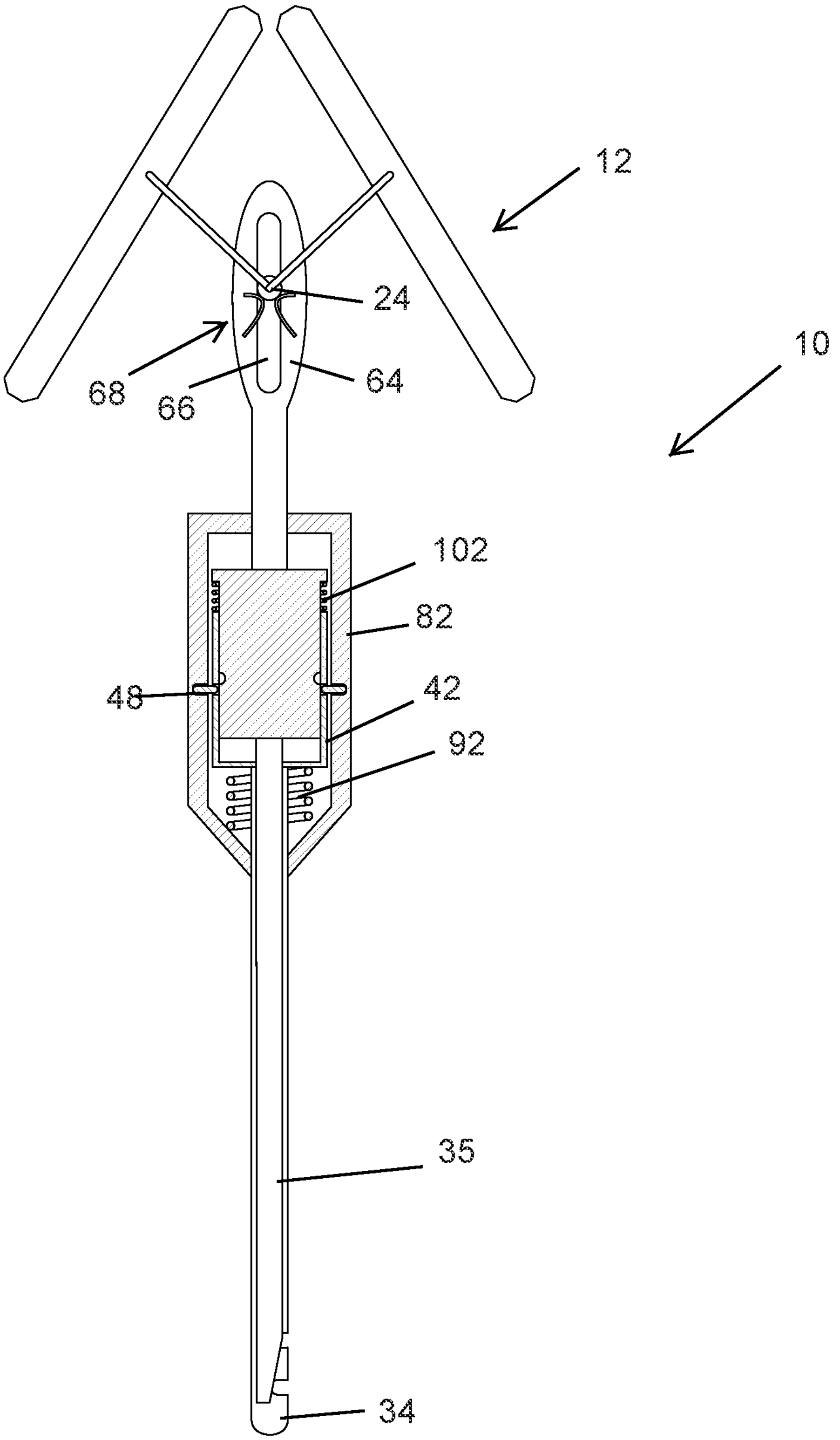

Referring to the embodiment shown in FIG. 5C, when in the arrestment position, the outer cannula hub 34 is locked into the outer hub case 82 by the at least one spring-loaded detent pin 48. As the drive pin 24 reaches the arrestment point, it compresses the spring gate 68 and the mid-outer curvature of the needle 54 is seated in the grooved recess 80 on the tapered face 78 on the distal push rod portion 62. In the arrestment position, needle 54 is held firmly while the first and second opposed handle bodies 18*a*, 18*b* are squeezed together (FIG. 5C). The inner rod hub 72 is free to slide within the hollow, concentric interior 86 of the outer cannula hub 82, which is locked into outer hub case 82 via the detent pins 48. The tapered face 78 on the distal push rod portion 62 is firmly pressed against the needle 54. The compression of the tapered face 78 and needle 54 against the interior surface 58 of lobe 56 between the distal fenestrations 50*a*, 50*b* has the needle 54 in the fully locked position. At the arrestment point, handle pressure can be reduced and there is concomitant retraction of the inner push rod 35. The outer cannula hub 42 position has not changed. The inner rod hub 72 travels freely in the hollow interior 46 of the outer cannula hub 42.

At the arrestment point, the inner push rod 35 is at its most distal point. The tapered face 78 on distal push rod portion 76 is of the appropriate dimension and shape to lock the needle 54 in to a position to pass the suture 55. The needle holder could be used conventionally, while preserving the ability for snap-back activation, if desired, by over-squeezing the first and second opposed handle bodies 18*a*, 18*b*. The arrestment point is the position of the first and second opposed handle bodies 18*a*, 18*b* where the inner push rod 35 exerts adequate compression force on the needle 54 to position it firmly so that the needle can be driven, or "thrown" through tissue or a graft material by the user manipulating the device.

At the arrestment point, the inner push rod 35 advancement is stopped by the combination of compression of the first spring 92 in the distal end 90 of the outer hub case 82 and the lateral spring gate 68 on the flattened portion 64 of the inner push rod 35 in which the drive pin 24 rides in slot 66. The tapered face 78 on the distal push rod portion 62 advances and firmly holds the needle 54. The second spring 102 uncompressible, or substantially uncompressible. The detent pin 48 follows the outer profile of the inner rod hub 72. The compressive state of first spring 90 is unchanged. The working length between the distal end 82 of outer hub case 82 and the distal end 40 of the outer cannula hub 34 is unchanged. Openings 50*a*, 50*b* are blocked by the greatest cross-section of the tapered face 78.

Figure 5D:
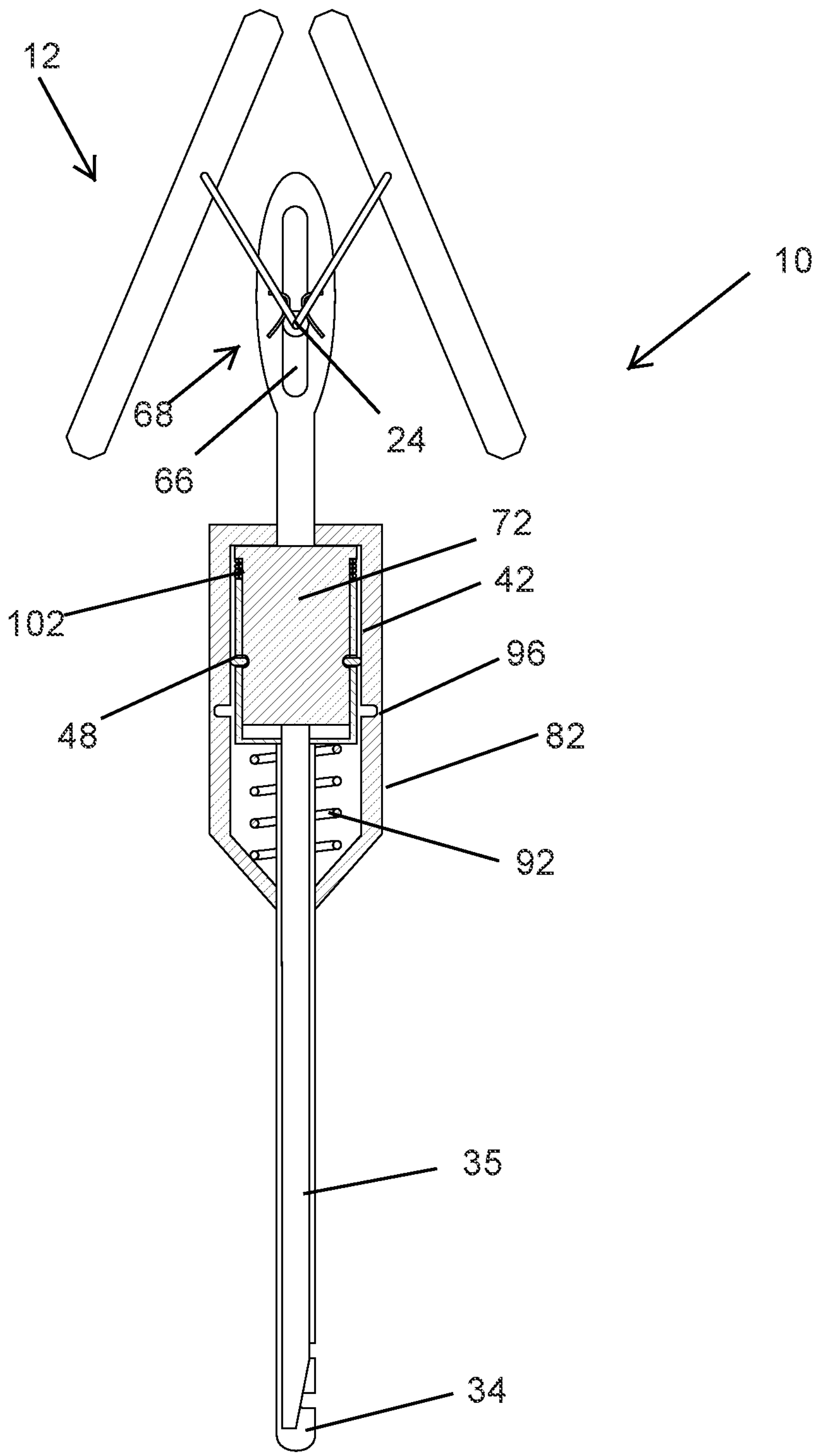

Referring to the embodiment shown in FIG. 5D, when in the snap-back position, the first and second opposed handle bodies 18*a*, 18*b* are "over-squeezed" or squeezed beyond the arrestment point such that the drive pin 24 squeezes past the spring gate 68 and is distal of a distal end 106 of the spring gate 68. First spring 92 disposed within the hollow interior 86 of the outer hub case 82 at the distal outer hub case portion 90 mechanism causes a rapid retraction of the two-piece shaft assembly toward the handle assembly 12 with the curved suture needle 54 in the fully compressed lock position (FIG. 5D). Each at least one spring-loaded detent pin 48 housed in the outer cannula hub 34 may have a radially inner end 108 and a radially outer end 110, a central flange 112 and a spring 114 disposed around the detent pin 48 between the central flange 112 and the radially outer end 110. Alternatively to the illustrated coil spring 114, a metal ribbon or wire, e.g. made of a cobalt alloy wire such as ELGILOY or another spring steel, shaped, coiled or bent to provide a spring force could be used. The radially outer end 110 of each detent pin 48 is released from the hold-point recesses 96 in the side wall 84 of the outer hub case 82. The radially inner end 108 of the detent pin 48 engages the at least one recess or groove 100 of the inner rod hub 72. This joins, or in some cases locks, the outer cannula hub 42 and the inner rod hub 72 together. The outer hollow cannula 34 is mounted into the outer cannula hub 42 and the inner push rod 35 is mounted on and through the inner rod hub 72. With outer cannula hub 42 and inner rod hub 72 joined together, the first spring 92 in the distal end 90 of the outer hub case 82 drives this joined hub 42, 72 and thus the outer hollow cannula 34 and the inner push rod 35, with the curved suture needle 54 in the locked position, retract rapidly towards the first and second opposed handle bodies 18*a*, 18*b*.

Once the needle 54 is driven through the surgical target, whether by snap-back activation from over-squeezing the first and second opposed handle bodies 18*a*, 18*b* or through wrist supination by the user, the first and second opposed handle bodies 18*a*, 18*b* are uncompressed, the inner push rod 35 retracts toward the first and second opposed handle bodies 18*a*, 18*b*, thereby releasing the needle 54.

When over-squeezed, the first spring 92 in the distal end 90 of the outer hub case 82 and the second spring 102 at the proximal end 88 of the outer hub case 82 are fully compressed. There is in-line mechanical contact of the inner rod hub 72 with the outer cannula hub 42. At this moment, the outer cannula hub 42 is advanced forward (distally). The radially outer end 110 of the detent pin 48 engages the recesses the at least one hold-point recess 96 in the outer hub case 82. Each hold-point recess 96 may include axially arranged, tear-drop risers 116 which create an abrupt, discreet release on the detent pins 48, while preventing any unintended re-engagement of the detent pins 48 during snap-back activation. Influenced by the tear-drop risers 116, longitudinal axis movement of the unitized elements of the outer cannula hub 42 and the inner rod hub 72, causes the detent pins 48 to release from the hold-point recesses 96. The detent pins 48 rapidly spring completely free from the outer hub case 82, through the outer cannula hub 42 and into at least one groove or recess 100 on the outer surface of the inner rod hub 35. This joins the outer cannula hub 42 and the inner rod hub 72. The position of the joined outer cannula hub 42 and inner rod hub 72 is such that the needle 54 is held firm in a "throwable" position.

The locked, unitized outer cannula hub 42 and inner solid rod hub 72 spring back proximally toward the handle assembly 12 due to the de-compression of the first spring 92 in the distal end 90 of the outer hub case 82 that contacts the distal end 40 of the outer hollow cannula 34. This "snap-back" action causes the tip of the needle 54 to traverse through tissue or graft material in a discreet, unidirectional manner (FIG. 5D).

In various embodiments, laterally opposed springs 70*a*, 70*b*, provide resistance to allow the drive pin 24 to advance the inner push rod 35. A point of high resistance is reached when spring 92 in the distal end 90 of the outer hub case 82 is compressed. Additional hand pressure, or over-squeezing beyond this arrestment point, overcomes the spring force of spring gate 68. The drive pin 24 slips past the spring gate 68 and the joined hub 42, 72 retracts rapidly toward the handle assembly 12. Once past the spring gate 68, the drive pin 24 can travel freely. This free travel minimizes resistance to the snap-back action and may reduce recoil to the handle assembly 12. Other embodiments, such as the embodiment of FIGS. 11A-11F, described herein may also utilize a spring gate 68 to facilitate snap-back action.

The geometry of the dual slotted fenestrations 50*a*, 50*b* may cradle the needle 54 in a semi-constrained position such that the greatest point for needle free fall-out is in the positive gravity positon without handle compression. The combined mechanism of the dual slotted fenestrations 50*a*, 50*b* and the relative position of the tapered face 78 apply a variable circumferential pressure to the curved suture needle. Independent in-situ needle repositioning is accomplished by varying the circumferential pressure.

In certain embodiments, the two-piece shaft assembly including elongate body 28 may be configured to rotate radially 360 degree relative to the handle assembly 12 at the distal end 16 of the handle assembly.

In further embodiments, the two-piece shaft assembly may be constructed with material of varying malleability-. The two-piece shaft assembly can be bayoneted, straight or angled.

The two-piece shaft assembly can be reusable. For example, embodiments may be made from surgical grade stainless steel which would allow for sterile reprocessing and more than one use. Other embodiments may be fully disposable.

Referring to the embodiments shown in FIGS. 7A-7F, there are several possible handle attachment point options. The figures shows examples of the handle assemblies 110, 210, 310 attached to pivot points on the outer case hub or a split rail mount option.

Devices in accordance with this disclosure permit conventional suturing (wrist supination) or when restricted by in-situ obstacles, activation of a snap-back deployment that passes the needle 54 in a rapid, precise, prescribed manner. Devices in accordance with this disclosure permit multiple needles 54 to be re-loaded on to the instrument throughout the surgery. In certain embodiments, in order to reset the needle holder device 10 after use, a user may grasp the outer hollow cannula 34 anywhere along its working length and pull distally while holding the outer hub case 82, the unitized outer cannula hub 42 and inner rod hub 72 are advanced distally. The detent pins 48 are aligned with the recess 96 in the outer hub case 82. The dual fenestrations are unrestricted. The pulling action forces the drive pin 24 back through and proximal the spring gate 68. Devices in accordance with this disclosure allow current commercially available needle and suture combinations to be used.

With reference to FIGS. 11A-11F, in some embodiments, a suture needle holder device 400 may have an outer hub case 482, detent pins 448, an outer cannula hub 442 having recesses 496, inner push rod 435 and an inner rod hub 472. Each detent pin 448 may have a spiral groove or channel 401 around its outer surface. The inner rod hub 472 has a follower 403 that rests in groove 401. The relationship between the detent pin 401, the grooves 401 and the follower 403 of the inner rod are kept in concert due to the spring force in the distal hub case and the action of the handles. This arrangement translates the longitudinal movement of the inner rod 435 to a lateral movement of a detent pin 448. The detent pin's position is being actively driven rather than being spring activated. Unnumbered elements are the same or similar to elements disclosed in the embodiments of FIGS. 2B, 3A and 5A-6.

Figure 11A:
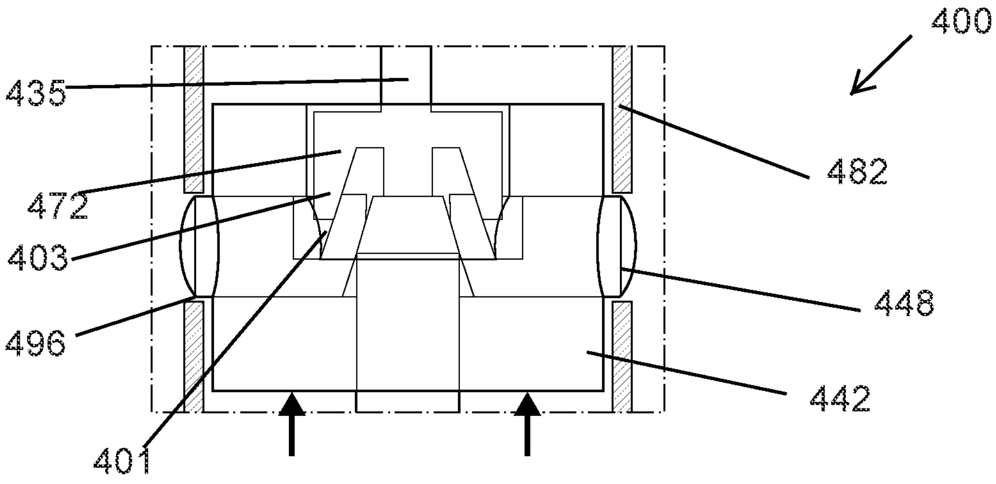
FIGS. 11A, 11B, 11C, 11D, 11E and 11F, show partial views of the needle holder according to various embodiments of the disclosure in open, closing, arrestment point, snap-back, return to reset and rest positions, respectively.

FIG. 11A shows an open position wherein the outer cannula hub 442 is locked into outer hub case 482 by the detent pins 448. Each follower 403 is not fully engaged within groove 401. The drive post in the longitudinal slot is advancing towards the spring gate and the dual fenestrations are opened and receptive to needle placement.

Figure 11B:
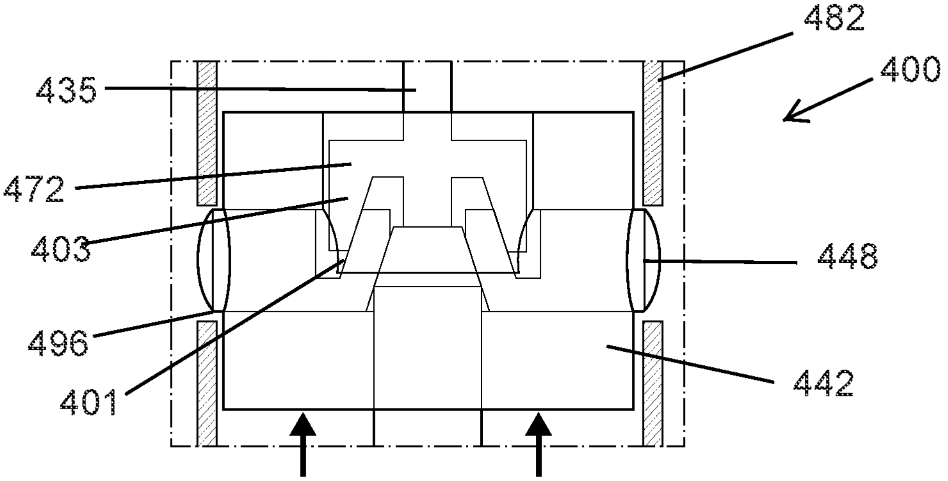

FIG. 11B shows a closing position wherein the outer cannula hub 442 is still locked into outer hub case 482 by the detent pins 448. The detent pins 448 are retracting from the recess 496 in the outer hub case 482. The drive post in the longitudinal slot is contacting the spring gate and the dual fenestrations are closed and needle is held firm.

Figure 11C:
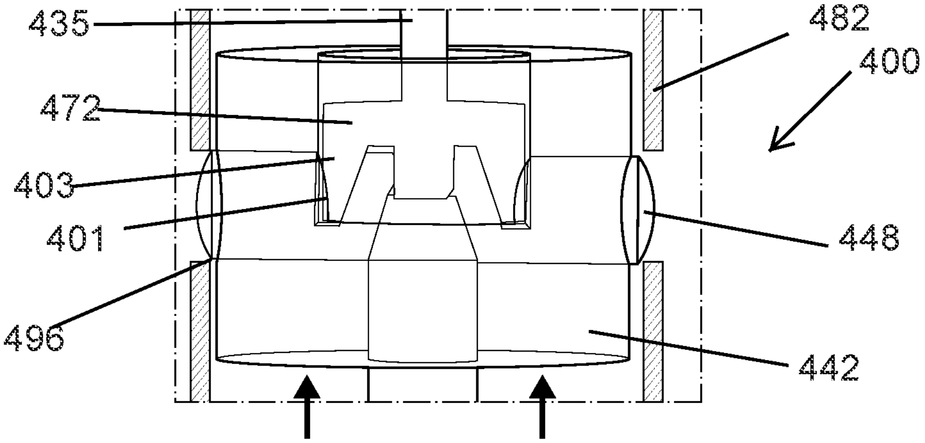

FIG. 11C shows an arrestment position wherein the outer cannula hub 442 is still locked into outer hub case 482 by the detent pins 448. Each follower 403 is fully engaged within groove 401. The detent pins 448 are retracting from the recess 496 in the outer hub case 482. The drive post in the longitudinal slot is at the point of maximum resistance in the spring gate and the dual fenestrations are closed and needle is held firm.

Figure 11D:
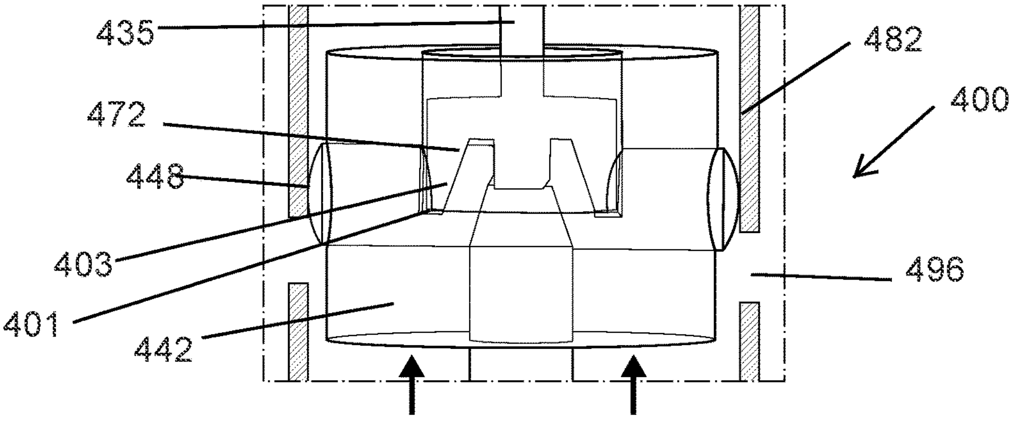
Figure 11E:
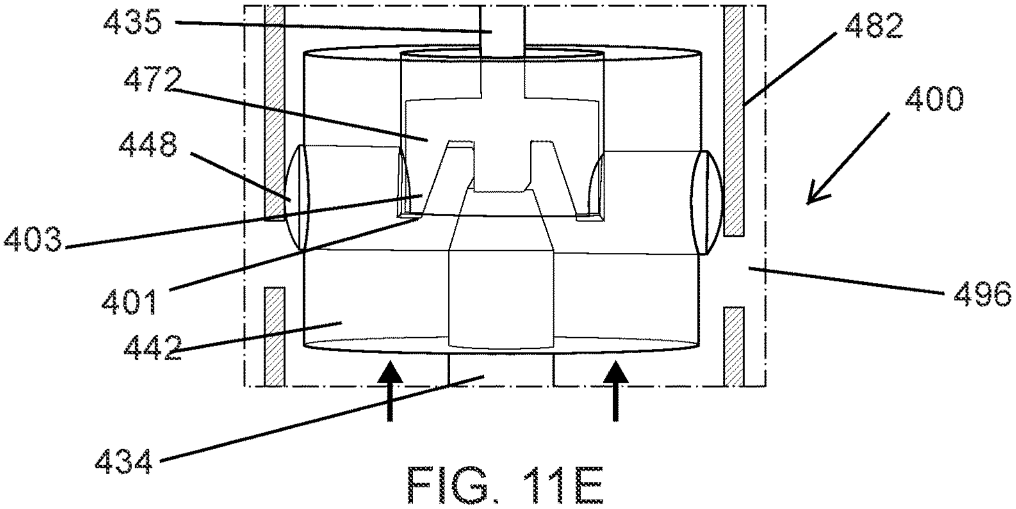
Figure 11F:
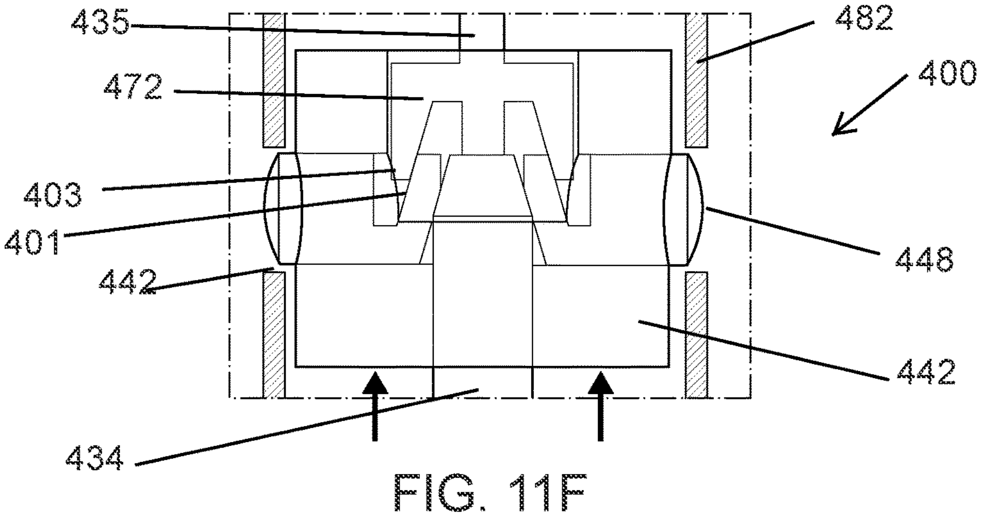

FIG. 11D shows a snap-back position wherein the outer cannula hub 442 is no longer locked into outer hub case 482 by the detent pins 448 and is unitized with the inner rod hub 472. The detent pins 448 are retracted from the recess 496 in the outer hub case 482. The first spring in the distal end of the outer hub case 482 drives the unitized outer cannula hub 442 and inner rod hub 472 proximally. The drive post in the longitudinal slot is distal to the spring gate and the dual fenestrations are closed and needle is held firm.

11E shows a return to reset position, wherein a user may grasp the outer hollow cannula 434 anywhere along its working length and pull distally, the unitized outer cannula hub 442 and inner rod hub 472 are advanced distally.

11F shows a reset position, the detent pins 448 are aligned with the recess 496 in the outer hub case 482. The dual fenestrations are unrestricted. The pulling action forces the drive pin back through and proximal the spring gate. Each follower 403 is disengaged from groove 401.

In some embodiments of using embodiments of the disclosure, a method of suturing may include the step of providing a suture needle holder device 10 which may include a handle assembly 12 comprising opposed handle bodies 18*a*, 18*b* operatively connected to a drive pin 24; an elongate body 28 connected with the handle assembly 12 and comprising an outer hollow cannula 34 comprising distal hollow cannula end portion 40 including at least two fenestrations 50*a*, 50*b* comprising an entrance fenestration and an exit fenestration and a suture release slot 52, and an inner push rod 35 operatively connected to the drive pin 24 and comprising a distal push rod portion 40 comprising a tapered face 78; an outer hub case 82 at a proximal end 30 of the elongate body 28. The method may further include the steps of inserting a curved suture needle 54 through the entrance fenestration 50*a* such that a distal tip of the needle 54 extends through the exit fenestration 50*b*, wherein the suture needle holder device 10 is an open position and the inner push rod 35 is proximal to the entrance and exit fenestrations 50*a*, 50*b*; compressing the handle assemblies 18*a*, 18*b* together until the tapered face 78 of the inner push rod 35 engages and locks the curved suture needle 54, placing the distal hollow cannula end portion 40 of the suture needle holder device 10 adjacent tissue to be sutured; over-compressing the handle assemblies 18*a*, 18*b* together retracting the outer hollow cannula 34 and inner push rod 35 proximally driving the curved suture needle into the tissue in a snap-back position of the needle holder device.

In some embodiments, a proximal push rod portion of the inner push rod 35 may include a longitudinal slot and a spring gate comprising laterally opposed springs disposed within the longitudinal slot 66, the drive pin may be configured for longitudinal displacement within the longitudinal slot 66, wherein the step of compressing the handle assemblies together further comprises driving the drive pin distally within the longitudinal slot 66.

In some embodiments, the inner push rod 35 includes an inner rod hub and 72 the outer cannula hub 34 includes an outer cannula hub 42 at proximal end thereof, wherein when in the open position, the drive pin 24 may be disposed within the longitudinal slot 66 proximal of the spring gate 68, and the outer cannula hub 34 is locked into the outer hub case 82 by at least one spring-loaded detent pin 48.

In some embodiments, when in the closing position, the first and second opposed handle bodies 18*a*, 18*b* are in a compressed position, the drive pin 24 may be configured to engage a proximal end of the spring gate 68, and the outer cannula hub 42 is locked into the outer case 82 via the at least one spring-loaded detent pin 48. In some embodiments, when in an arrestment position, the outer cannula hub 42 is locked into the outer case 82 by the at least one spring-loaded detent pin. In some embodiments, the tapered face 78 of the inner push rod 35 may further include a longitudinal grooved recess 80 configured to seat the curved suture needle 54, when in the arrestment position.

In some embodiments, the inner rod hub 72 may further include at least one groove or recess 100, 200, 300 on the inner rod hub configured to engage the at least one spring-loaded detent pin 48, wherein the inner rod hub 72 and the outer cannula hub 42 are locked together by the at least one spring-loaded detent pin 48 when in the when the needle holding device is in the snap-back position. In some embodiments, when in the snap-back position, the drive pin 48 is distal of the spring gate 68.

It should be noted that the use of particular terminology when describing certain features or embodiments of the disclosure should not be taken to imply that the terminology is being re-defined herein to be restricted to include any specific characteristics of the features or embodiments of the disclosure with which that terminology is associated. Terms and phrases used in this application, and variations thereof, especially in the appended claims, unless otherwise expressly stated, should be construed as open-ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "such as" should be interpreted as "such as, without limitation"; the term "includes" should be interpreted as "includes but is not limited to"; the term "example" is used to provide exemplary instances of the item in discussion, not an exhaustive or limiting list thereof, and should be interpreted as "example, but without limitation"; adjectives such as "known," "normal," "standard," and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the present disclosure, but instead as merely intended to highlight alternative or additional features that may or may not be utilized in a particular embodiment.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. The terms "about" or "approximate" and the like are synonymous and are used to indicate that the value modified by the term has an understood range associated with it, where the range may be ±20%, ±15%, ±10%, ±5%, or ±1%. The term "substantially" is used to indicate that a result (e.g., measurement value) is close to a targeted value, where close may mean, for example, the result is within 80% of the value, within 90% of the value, within 95% of the value, or within 99% of the value. Also, as used herein "defined" or "determined" may include "predefined" or "predetermined" and/or otherwise determined values, conditions, thresholds, measurements, and the like.

What is claimed is:

1. A suture needle holder device comprising:

a handle assembly comprising a proximal handle end, a distal handle end, and first and second opposed handle bodies each pivotally connected to a handle drive arm at a first end of each handle drive arm, wherein the handle assembly further comprises a common drive pin pivotally connected to a second end of each drive arm;

an elongate body connected with the handle assembly at the distal handle end, the elongate body comprising a proximal elongate body end portion and a distal elongate body end portion, the elongate body comprising:

an outer hollow cannula comprising a hollow interior, a proximal hollow cannula end portion and a distal hollow cannula end portion; wherein the proximal hollow cannula end portion comprises a cannula hub comprising a cylindrical side wall, a hollow interior, and at least one spring-loaded detent pin disposed radially through corresponding radial through holes in the cylindrical side wall, wherein the distal hollow cannula end portion comprises at least two fenestrations and a suture release slot connecting the at least two fenestrations, and wherein a first one of the at least two fenestrations is configured as a suture needle entry point, and a second one of the at least two fenestrations is configured as a suture needle exit point;

an inner push rod comprising a proximal push rod portion and a distal push rod portion, the inner push rod arranged for longitudinal displacement within the hollow interior of the outer hollow cannula, wherein the proximal push rod portion comprises a longitudinal slot and a spring gate comprising laterally opposed springs disposed within the longitudinal slot, wherein the drive pin is configured for longitudinal displacement within the longitudinal slot of the inner push rod upon compression of the first and second handle bodies towards one another, the inner push rod further comprising an inner rod hub comprising a proximal inner rod hub portion and a distal inner rod hub portion and configured for longitudinal displacement within the hollow interior of the cannula hub, wherein the distal push rod portion comprises a wedge shape comprising a tapered face configured to engage a curved suture needle inserted between the suture needle entrance point and the suture needle exit point; and an outer hub case comprising a side wall, a hollow interior, a proximal outer hub case portion and a distal outer hub case portion, wherein the cannula hub and the inner rod hub are arranged for longitudinal displacement within the hollow interior of the outer hub case, and a first spring is disposed within the hollow interior of the outer hub case at the distal outer hub case portion;

wherein the suture needle holder device is configured to be operable between an open position wherein the inner push rod is proximal to the at least two fenestrations, a closing position wherein the tapered face of the inner push rod is configured to engage the curved suture needle, an arrestment position wherein the inner push rod is disposed at the most remote distal position within the outer hollow cannula, and a snap-back position wherein the first spring within the distal outer hub case portion causes a retraction of the outer hollow cannula and inner push rod.

2. The suture needle holder device of claim 1, when in the open position, the first and second opposed handle bodies are in an un-compressed position, the drive pin is disposed within the longitudinal slot proximal of the spring gate, and the outer cannula hub is locked into the outer hub case by the at least one spring-loaded detent pin.

3. The suture needle holder device of claim 2, wherein an inner surface of the sidewall of the outer hub case further comprises at least one recess configured to engage the at least one spring-loaded detent pin, when in the open position.

4. The suture needle holder device of claim 1, wherein the inner rod hub further comprises a proximal flange on the proximal inner rod hub portion and at least one groove or recess on the distal inner rod hub on an outer surface of the distal inner rod portion configured to engage the at least one spring-loaded detent pin, and further comprising a second spring disposed within the hollow interior of the outer hub case at the proximal outer hub case portion between the proximal flange and the cannula hub.

5. The suture needle holder device of claim 4, when in the closing position, the first and second opposed handle bodies are in a compressed position, the drive pin is configured to engage a proximal end of the spring gate, and the outer cannula hub is locked into the outer case via the at least one spring-loaded detent pin.

6. The suture needle holder device of claim 1, when in the arrestment position, the outer cannula hub is locked into the outer case by the at least one spring-loaded detent pin.

7. The suture needle holder device of claim 6, wherein the tapered face of the inner push rod further comprises a longitudinal grooved recess configured to seat the curved suture needle, when in the arrestment position.

8. The suture needle holder device of claim 1, when in the snap-back position, the drive pin is distal of the spring gate.

* * * * *